July 31, 1923.

Re. 15,663

J. O. LANDIS

MANICURE IMPLEMENT

Original Filed April 19, 1919

WITNESSES

O. Mauk

P. H. Pattison.

INVENTOR

J. O. LANDIS

BY Munn & Co

ATTORNEYS

Reissued July 31, 1923. Re. 15,663

UNITED STATES PATENT OFFICE.

JOHN OLIN LANDIS, OF WAYNESBORO, PENNSYLVANIA.

MANICURE IMPLEMENT.

Original No. 1,324,677, dated December 9, 1919, Serial No. 291,314, filed April 19, 1919. Application for reissue filed March 15, 1923. Serial No. 625,269.

*To all whom it may concern:*

Be it known that I, JOHN OLIN LANDIS, a citizen of the United States, and a resident of Waynesboro, in the county of Franklin and State of Pennsylvania, have invented a new and Improved Manicure Implement, of which the following is a full, clear, and exact description.

The present invention relates to new and useful improvements in manicuring implements and pertains more particularly to small tools especially adapted for trimming nails.

The object of the present invention is to provide a device of this character which in its initial manufacture is both simple and cheap.

A further object of the invention is to provide a device of this character in which the cutting edge may from time to time be renewed.

With the above and other objects in view, reference is had to the accompanying drawings, in which—

Figure 1:
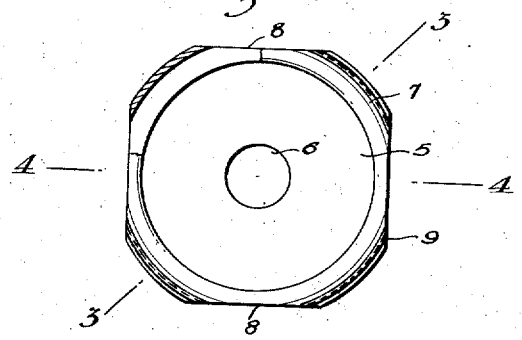
Figure 1 is a top plan view of a device constructed in accordance with the present invention.
Figure 2:
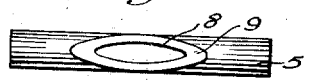
Fig. 2 is an edge view thereof.

Referring more particularly to the drawings, the reference character 5 designates a metal plate, the center of which is provided with an opening 6, which in the present instance is shown as round but which may be made in any desired form or the same may be omitted without affecting the scope of the invention.

Figure 3:
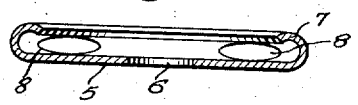
Fig. 3 is a transverse sectional view on the line 3—3 of Fig. 1.
Figure 4:
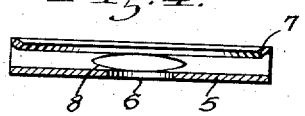
Fig. 4 is a transverse sectional view on the line 4—4 of Fig. 1.

The reference character 7 designates an annular flange formed on the marginal edge of the plate 5, and as best seen in Fig. 3, the flange 7 is circular in cross section, but may be in the form of a channel or elliptical in form.

Formed in the flange 7 about the periphery of the plate 5, are a plurality of cutting elements 8.

In making the device, a flat circular disk of metal, preferably steel, is employed, and said disk may or may not be perforated, as at 6.

After the disk has been thus formed, it is subjected to the action of suitable dies to form the annular marginal flange 7, which flange is subsequently subjected to suitable mechanism for bending or curling its rim inward.

The disk with its flange formed as above described, is now put through any suitable hardening process, after which it may be polished for the purpose of imparting a finish thereto. The disk is now subjected to the action of a suitable grinding machine and the cutting elements 8 are formed by grinding through the flange 7, the disk being ground in such a manner that flat sides 9 are produced about its periphery. These sides may or may not be equidistantly spaced about the disk, as desired.

From the foregoing it will be seen that the present invention not only provides a device which is simple and cheap in manufacture, but contemplates a device in which the cutting elements may be renewed from time to time by merely subjecting the flat faces to the action of a suitable abrading material.

Having thus described the invention, what is claimed is:

1. A device of the character described comprising a metal disk provided on its edge with a continuous annular flange of substantially circular form in cross section, said flange having flat ground surfaces about its periphery, said ground surfaces extending entirely through the flange to provide a plurality of cutting members.

2. A device of the character described comprising a perforated metal disk provided on its edge with a continuous annular flange of substantially circular form in cross section, said flange having flat ground surfaces at equidistantly spaced intervals about its periphery, said ground surfaces extending entirely through the flange to provide a plurality of equidistantly spaced continuous cutting members.

JOHN OLIN LANDIS.